(12) United States Patent
Styrbjorn Fallman et al.

(10) Patent No.: US 12,383,663 B2
(45) Date of Patent: Aug. 12, 2025

(54) PERITONEAL DIALYSIS SYSTEM HAVING CARBON DIOXIDE INJECTION TO INHIBIT/REMOVE CALCIUM CARBONATE

(71) Applicants: BAXTER INTERNATIONAL INC., Deerfield, IL (US); BAXTER HEALTHCARE SA, Glattpark (CH)

(72) Inventors: Oskar Erik Frode Styrbjorn Fallman, Lund (SE); Michael Pettersson, Malmo (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 433 days.

(21) Appl. No.: 18/081,375

(22) Filed: Dec. 14, 2022

(65) Prior Publication Data

US 2023/0201436 A1   Jun. 29, 2023

Related U.S. Application Data

(60) Provisional application No. 63/293,383, filed on Dec. 23, 2021.

(51) Int. Cl.
*A61M 1/28* (2006.01)
*A61M 1/16* (2006.01)

(52) U.S. Cl.
CPC ............ *A61M 1/282* (2014.02); *A61M 1/166* (2014.02); *A61M 1/1664* (2014.02); *A61M 1/1686* (2013.01); *A61M 1/1688* (2014.02); *A61M 1/28* (2013.01); *A61M 1/287* (2013.01); *A61M 2202/0225* (2013.01); *A61M 2205/3331* (2013.01)

(58) Field of Classification Search
CPC .. A61M 1/166; A61M 1/1664; A61M 1/1686; A61M 1/1688; A61M 1/28; A61M 1/282; A61M 1/287; A61M 2202/0225; A61M 2205/3331
See application file for complete search history.

(56) References Cited

FOREIGN PATENT DOCUMENTS

EP   0437274 A1   7/1991
EP   1182264 B1   3/2006

OTHER PUBLICATIONS

English translation European Patent Application No. 0437274 A1 (1991).*
International Search Report from International Patent Application No. PCT/US2022/081526, mailed Apr. 17, 2023.

(Continued)

*Primary Examiner* — John Kim
(74) *Attorney, Agent, or Firm* — K&L Gates LLP

(57) ABSTRACT

A peritoneal dialysis ("PD") system includes a PD fluid pump; a disinfection loop including the PD fluid pump, the disinfection loop including PD fluid used for disinfecting the disinfection loop; and a carbon dioxide ($CO_2$), source positioned and arranged to supply $CO_2$ to the disinfection loop to inhibit and/or remove the production of calcium carbonate ($CaCO_3$) during a disinfection sequence. The PD system includes a control unit configured to open a valve to allow $CO_2$ to be supplied, wherein the control unit may use a lookup table or algorithm to determine the desired pressure or pressure increase.

16 Claims, 4 Drawing Sheets

(56) References Cited

OTHER PUBLICATIONS

Written Opinion from International Patent Application No. PCT/US2022/081526, mailed Apr. 17, 2023.
International Preliminary Report on Patentability and Written Opinion of the International Searching Authority for International Application No. PCT/US2022/081526 mailed Jun. 20, 2024.

* cited by examiner

PERITONEAL DIALYSIS SYSTEM HAVING CARBON DIOXIDE INJECTION TO INHIBIT/REMOVE CALCIUM CARBONATE

PRIORITY CLAIM

This application claims priority to and the benefit of U.S. Provisional Patent Application 63/293,383, filed Dec. 23, 2021, entitled "PERITONEAL DIALYSIS SYSTEM HAVING CARBON DIOXIDE INJECTION TO INHIBIT/REMOVE CALCIUM CARBONATE", the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste. In doing so, to the extent that deposits of calcium carbonate are created via disinfection, such deposits present a problem that may increase over time. A need exists accordingly for a PD system having a way to inhibit the production of calcium carbonate and/or to remove same if produced.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

The APD system and associated methodology of the present disclosure, on the other hand, convert much of the fluid carrying portions of its PD system into reusable components, which are disinfected after treatment. Fluid lines within the machine or cycler are reused. Disposable items remaining may include a drain line leading to a drain bag or house drain and one or more PD fluid container or bag, such as different dextrose or glucose level PD fluid containers and a last bag container, e.g., containing icodextrine. In an embodiment, a disposable filter is placed at the distal end of the patient line to provide a final stage of PD fluid filtration prior to delivery to the patient.

The APD system of the present disclosure incudes an APD cycler having a housing. At least one and perhaps three or more reusable PD fluid lines extend from the housing. When not connected to PD fluid containers or bags, the reusable PD fluid lines can be connected to disinfection connectors supported and provided by the housing. The reusable PD fluid lines may for example extend from a front of the housing and connect to disinfection connectors also provided at the front of the housing for ready access to the PD fluid lines. The reusable PD fluid lines may be color coded and/or keyed to match a colored or keyed connector of the PD fluid container or bag. The containers or bags may hold different dextrose or glucose level PD fluids, such as 1.36% glucose PD fluid, 2.27% glucose PD fluid, 3.86% glucose PD fluid and/or a last bag of a different formulation of PD fluid, such as icodextrin. The PD fluids may contain a bicarbonate component.

Inside the housing, reusable tubing runs from each of the reusable PD fluid lines, through a PD fluid supply valve for each PD fluid line, to a PD fluid inline heater. In an embodiment, each of the valves of the APD cycler is an electrically actuated valve having a reusable valve body that occludes (e.g., when unpowered) or allows (e.g., when powered) PD fluid to flow through the body. The PD fluid inline heater is also electrically actuated in one embodiment and is, for example, a resistive heater having a reusable heater body that accepts PD fluid for heating. The inline heater in an embodiment is able to heat PD fluid from room temperature to body temperature, e.g., 37° C., at a flowrate of at least 200 milliliters ("ml")/minute. A temperature sensor is located adjacent to the heater, e.g., downstream from the heater to provide feedback for temperature control.

Reusable tubing runs from the outlet of the PD fluid inline heater to an airtrap in one embodiment. Any of the tubing inside the housing of the cycler may be metal, e.g., stainless steel, or plastic, e.g., polyvinylchloride ("PVC") or a non-PVC material, such as polyethylene ("PE"), polyurethane ("PU") or polycarbonate ("PC"). In an embodiment, one or more level sensor is located adjacent to the airtrap so that a desired level or range of levels of PD fluid is/are maintained in the airtrap. A fluid line valve is located along a reusable fluid line downstream from the airtrap in an embodiment. At least one gas line valve located along at least one gas line may also be provided. The airtrap may be closed upstream by PD fluid supply valves to drain the airtrap when dictated by the output of the level sensors.

A reusable PD fluid pump is located within the cycler housing and includes a reusable pump body that accepts PD fluid for pumping. That is, the pump does not require the PD fluid to flow within a disposable item, such as a tube or cassette. The PD fluid pump may be an electrically operated piston pump, which is inherently accurate so that a separate PD fluid volume measurement apparatus, such as a flowmeter, balance chamber or an apparatus using the ideal gas law, is not needed. The PD fluid pump may alternatively be an electrically operated, gear or centrifugal pump, which may operate with a separate PD fluid volume measurement apparatus.

The PD fluid pump is controllable to pump to and from the patient at or below a pressure limit by controlling a level of current to the PD fluid pump. A positive patient pressure limit may for example be one to five psig (e.g., two psig (14 kPa)). A negative patient pressure limit may for example be −1.0 psig to −3.0 psig (e.g., −1.3 psig (−9 kPa)). The PD fluid pump is bidirectional and continuous in one embodiment, such that a single pump may be provided.

The APD cycler of the APD system of the present disclosure includes a control unit having one or more processor and one or more memory that receives signals or outputs from pressure sensors, temperature sensors and possibly a conductivity sensor and that processes the signals or outputs as feedback. The control unit uses pressure feedback to control the PD fluid pump to run at safe patient pressure limits during treatment and safe system limits during disinfection. The control unit uses temperature feedback to control the PD fluid heater to heat the fresh PD fluid to, e.g., body temperature.

The control unit also opens and closes the PD fluid valves in combination with the PD fluid pump and heater to run a priming sequence, a patient fill sequence, a patient drain sequence, and a disinfection sequence after a PD treatment, wherein each of the at least one reusable PD fluid supply line is connected to one of the at least one disinfection connectors, and wherein the reusable patient line is connected to the reusable patient line connector. The disinfection sequence readies the APD cycler for the next treatment. In an embodiment, unused PD fluid is heated after the final drain and is used for disinfection.

The use of unused PD fluid containing bicarbonate as a disinfection fluid can lead to the formation of calcium carbonate in the disinfected flowpaths and flow components of the PD machine or cycler (forming a disinfection loop). The present system accordingly includes a source carbon dioxide ($CO_2$), which is injected during disinfection to prevent and/or to remove the formation of calcium carbonate. The $CO_2$ source is placed in fluid communication via a $CO_2$ line controlled by a $CO_2$ valve in one embodiment.

The control unit is programmed to run a sequence that in one embodiment relies on a table stored in one or more memory of the control unit. The table in one implementation sets a pressure increase due to the $CO_2$ injection or an overall pressure to be achieved by the $CO_2$ injection as a function of at least one of solution bicarbonate composition and/or disinfection temperature setting. Generally, the more bicarbonate present in the PD fluid, the higher the pressure needed due to the injected $CO_2$ gas. And generally, the higher the disinfection PD fluid temperature, the higher the pressure needed due to the injected $CO_2$ gas. Experiments and/or calculations are performed varying bicarbonate levels against varied disinfection temperatures to determine how much $CO_2$ gas pressure is needed to effectively block the formation of calcium carbonate precipitation, while efficiently using $CO_2$ gas, so as not to waste $CO_2$, and so that the $CO_2$ source may be of a reasonable size, while still providing many disinfection sequences' worth of $CO_2$.

The table in another implementation may represent the mole fraction of $CO_2$, which depends on the type of disinfection fluid, e.g., PD fluid, the temperature of the PD fluid and the pressure of the PD fluid, wherein the mole fraction values populate the spaces corresponding to a given temperature and pressure. A desired amount of $CO_2$ is determined from a chemical equation in which the addition of $CO_2$ to water contained in the disinfecting PD fluid creates carbonic acid, which when combined with calcium carbonate causes a chemical reaction that breaks the calcium carbonate into calcium and bicarbonate ions, which are suspended in the PD fluid and carried to drain. The control unit here uses the table to determine how much the disinfection fluid pressure needs to be increased via the injection of $CO_2$ to achieve a desired amount of $CO_2$ (e.g., in mmol). In an embodiment, a separate mole fraction table is stored and is accessible by the control unit for each possible disinfection fluid or PD fluid, e.g., one for 1.36% glucose PD fluid, another for 2.27% glucose PD fluid and a third for 3.86% glucose PD fluid, etc.

A first step for introducing $CO_2$ into the disinfection loop occurs when treatment has been completed and it is time for the control unit to perform disinfection. Prior to beginning the disinfection sequence, the control unit in one embodiment with the $CO_2$ valve closed, the PD fluid pump not actuated and the heater unenergized, accesses a lookup table (or corresponding algorithm) that sets a pressure to achieve (or pressure increase) as a function of the bicarbonate level in the PD fluid used for disinfection and/or a disinfection fluid temperature. The control unit in another embodiment takes initial pressure and temperature measurements to obtain an initial $CO_2$ mole fraction value from a stored table for the particular disinfecting fluid used. An optional pH sensor or $CO_2$ sensor may be provided and used alternatively or additionally to determine the $CO_2$ mole fraction, however, the lookup table for the particular disinfection fluid will suffice and eliminate the need for the extra sensors. In either embodiment, a pressure to achieve, or a pressure increase, due to $CO_2$ gas injection is obtained and used.

A second step for introducing $CO_2$ occurs with the PD fluid pump not actuated and the heater unenergized. The control unit causes the $CO_2$ valve to open, allowing $CO_2$ to be injected into the PD fluid within the disinfection loop. The control unit may cause the $CO_2$ to be pulsed or injected continuously. In either case, the control unit monitors the output of pressure sensor and stops injecting $CO_2$ when the pressure achieves the needed pressure increase or overall pressure as determined from either of the lookup tables discussed herein.

A third step for introducing $CO_2$ occurs with the control unit causing the PD fluid heater to be energized and the PD fluid pump to be actuated to circulate heated, disinfection fluid (PD fluid) about the disinfection loop in any of the alternative manners described herein and at the elevated $CO_2$ pressure. The heated disinfection fluid circulation takes place for a designated amount of time. During this time, the presence of the designated amount of $CO_2$ at the elevated pressure prevents or removes calcium carbonate ($CaCO_3$) according to the chemical reaction described herein.

A fourth, perhaps optional, step for introducing $CO_2$ occurs with the control unit causing the PD fluid heater to be de-energized but continuing to allow the fluid pump to circulate cooled-down PD fluid. During a cool down period, the control unit monitors the output of the pressure sensor to see if the output returns to the pressure level prior to heating. If perhaps some leak of $CO_2$ has occurred and the pressure falls below the $CO_2$ injected pressure, then control unit may cause the $CO_2$ valve to open to allow additional $CO_2$ to be injected, e.g., so as to re-reach a desired pressure increase above the initial, starting pressure. The ammonia and/or $CO_2$ sensor if provided may be used additionally or alternatively here to help meter additional $CO_2$ into the disinfection loop.

In light of the disclosure set forth herein, and without limiting the disclosure in any way, in a first aspect of the present disclosure, which may be combined with any other aspect, or portion thereof, a peritoneal dialysis ("PD") system includes a PD fluid pump; a disinfection loop including the PD fluid pump, the disinfection loop including PD fluid used for disinfecting the disinfection loop; and a carbon dioxide ($CO_2$), source positioned and arranged to supply $CO_2$ to the disinfection loop to inhibit and/or remove the production of calcium carbonate ($CaCO_3$) during a disinfection sequence.

In a second aspect of the present disclosure, which may be combined with any other aspect, or portion thereof, the PD system includes a $CO_2$ valve located between the disinfection loop and the $CO_2$ source, the $CO_2$ valve opened to allow the $CO_2$ to be supplied to the disinfection loop.

In a third aspect of the present disclosure, which may be combined with any other aspect, or portion thereof, the PD system includes a control unit configured to cause the $CO_2$ valve to open to allow the $CO_2$ to pressurize the PD fluid to a desired pressure or pressure increase to inhibit and/or remove the production of calcium carbonate during the disinfection sequence.

In a fourth aspect of the present disclosure, which may be combined with any other aspect, or portion thereof, the PD system includes at least one pressure sensor outputting to the control unit, the control unit configured to monitor the at least one pressure sensor output to detect the desired pressure or pressure increase.

In a fifth aspect of the present disclosure, which may be combined with any other aspect, or portion thereof, the control unit is configured to use a lookup table to determine the desired pressure or pressure increase.

In a sixth aspect of the present disclosure, which may be combined with any other aspect, or portion thereof, the control unit stores a disinfection temperature to which the PD fluid is heated for the disinfection sequence, and wherein the desired pressure or pressure increase in the lookup table corresponds to the disinfection temperature.

In a seventh aspect of the present disclosure, which may be combined with any other aspect, or portion thereof, the PD system includes at least one temperature sensor outputting to the control unit, the control unit configured to monitor the at least one temperature sensor output to detect the disinfection temperature.

In an eighth aspect of the present disclosure, which may be combined with any other aspect, or portion thereof, the lookup table is specific to the type of PD fluid used for disinfection.

In a ninth aspect of the present disclosure, which may be combined with any other aspect, or portion thereof, the control unit knows a bicarbonate level for the PD fluid used for disinfection, and wherein the desired pressure or pressure increase in the lookup table corresponds to the bicarbonate level.

In a tenth aspect of the present disclosure, which may be combined with any other aspect, or portion thereof, the control unit is configured to take initial pressure and temperature readings prior to supplying $CO_2$ to the disinfection loop, the control unit further configured to determine the initial amount of $CO_2$ contained in the disinfection loop using the lookup table and the initial pressure and temperature readings.

In an eleventh aspect of the present disclosure, which may be combined with any other aspect, or portion thereof, the control unit is configured to use an algorithm to determine the desired pressure or pressure increase.

In a twelfth aspect of the present disclosure, which may be combined with any other aspect, or portion thereof, the control unit is configured to cause the $CO_2$ valve to open to allow the $CO_2$ to pressurize the PD fluid to the desired pressure or pressure increase prior to causing the PD fluid pump to run during the disinfection sequence.

In a thirteenth aspect of the present disclosure, which may be combined with any other aspect, or portion thereof, the control unit is configured to cause the $CO_2$ valve to open to allow the $CO_2$ to pressurize the PD fluid to the desired pressure or pressure increase while causing the PD fluid pump to run during the disinfection sequence.

In a fourteenth aspect of the present disclosure, which may be combined with any other aspect, or portion thereof, the PD system includes a PD fluid heater, and wherein the control unit is configured to cause the $CO_2$ valve to open to allow the $CO_2$ to pressurize the PD fluid to the desired pressure or pressure increase prior to causing the PD fluid heater to heat the PD fluid during the disinfection sequence.

In a fifteenth aspect of the present disclosure, which may be combined with any other aspect, or portion thereof, the PD system includes a PD fluid heater, and wherein the control unit is configured to cause the $CO_2$ valve to open to allow the $CO_2$ to pressurize the PD fluid to the desired pressure or pressure while causing the PD fluid heater to heat the PD fluid during the disinfection sequence.

In a sixteenth aspect of the present disclosure, which may be combined with any other aspect, or portion thereof, the control unit is configured to cause the $CO_2$ valve to open to allow the $CO_2$ to pressurize the PD fluid during a cool down period if a loss of pressure is detected by the control unit.

In a seventeenth aspect of the present disclosure, which may be combined with any other aspect, or portion thereof, any of the features, functionality and alternatives described in connection with any one or more of FIGS. 1 to 7 may be combined with any of the features, functionality and alternatives described in connection with any other of FIGS. 1 to 7.

It is accordingly an advantage of the present disclosure to provide a system for an automated peritoneal dialysis ("APD") cycler that helps to ensure that calcium carbonate production is inhibited or that calcium carbonate is cleaned and removed during disinfection.

It is another advantage of the present disclosure to provide a system for an APD cycler that efficiently uses carbon dioxide ($CO_2$) during disinfection to prevent or remove the development of calcium carbonate.

It is a further advantage of the present disclosure to provide a system for an APD cycler that helps to prevent the build-up of precipitates during disinfection.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Generally

Figure 1:
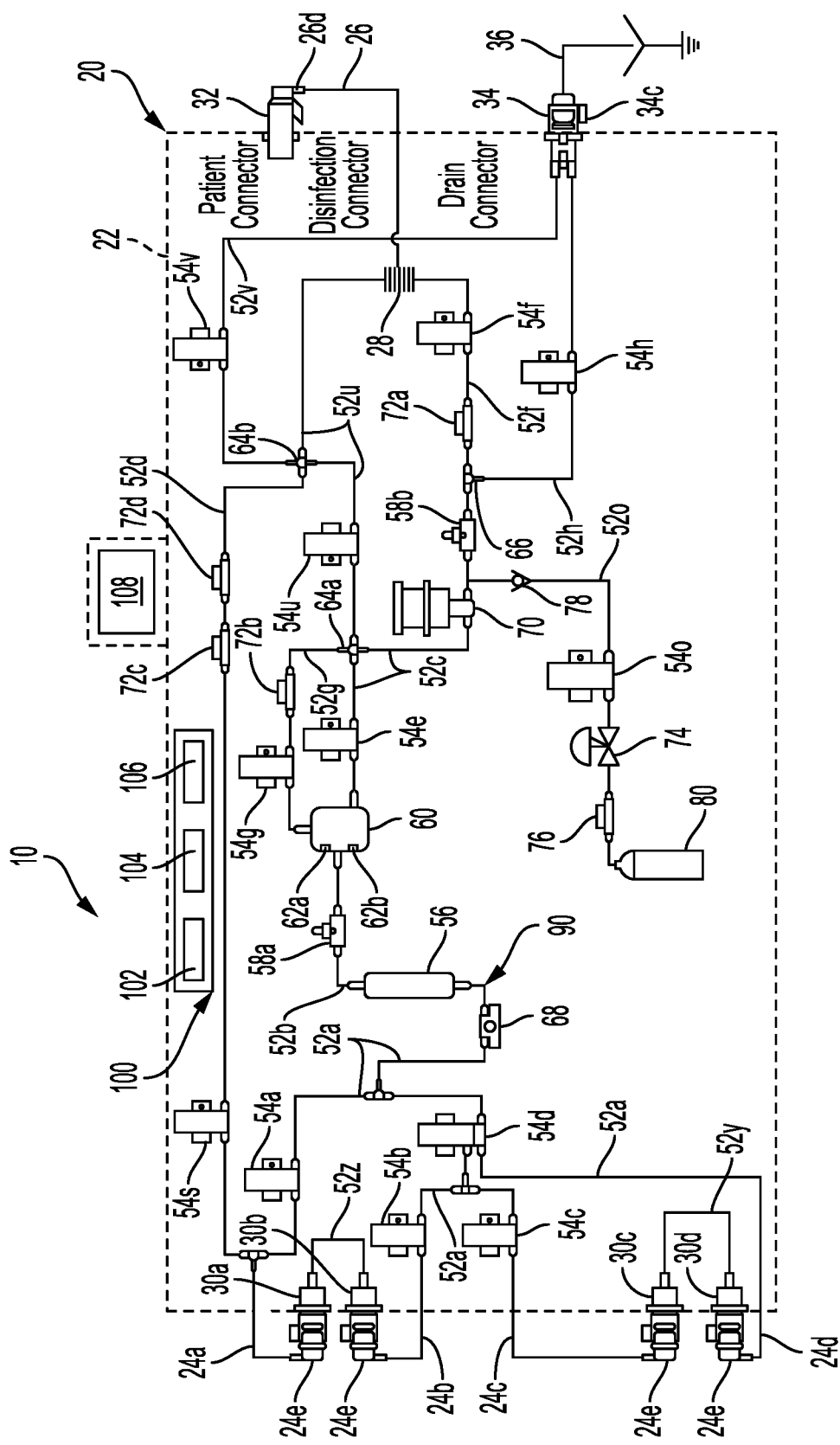
FIG. 1 is a schematic view of one embodiment of an automated peritoneal dialysis ("APD") machine or cycler and associated system of the present disclosure.

Referring now to the drawings and in particular to FIG. 1, automated peritoneal dialysis ("APD") system 10 and associated methodology of the present disclosure includes an APD machine or cycler 20. System 10 and cycler 20 attempt to eliminate disposable items as much as possible and instead provide the majority of its fluid carrying portions as reusable components, which are disinfected after treatment. Fluid lines within the machine or cycler are reused. In particular, FIG. 1 illustrates that cycler 20 includes a housing 22 from which reusable PD fluid supply lines 24*a* to 24*d* extend. FIG. 1 further illustrates that a reusable patient line 26 also extends from housing 22 of machine or cycler 20. Reusable patient line 26, which is typically longer than reusable PD fluid supply lines 24a to 24d, may be coiled or rolled up within the housing via a spool or hose reel 28 when reusable patient line 26 is not connected to a patient for treatment.

When not connected to PD fluid containers or bags, the reusable PD fluid supply lines 24a to 24d and patient line 26 can be connected to dedicated connectors supported and provided by housing 22. The reusable PD fluid supply and patient lines may for example extend from a front of housing 22 and connect to connectors also provided at the front of the housing for ready access to the PD fluid and patient lines. In the illustrated embodiment, distal ends 24e of reusable PD fluid supply lines 24a to 24d releasably attach in a fluid-tight manner to disinfection connectors 30a to 30d, respectively, provided at housing 22. Distal end 26d of reusable patient line 26 releasably attaches in a fluid-tight manner to patient line connector 32 provided at housing 22. Disinfection connectors 30a to 30d and patient line connector 32 are configured in one embodiment to close or shut automatically when reusable PD fluid supply lines 24a to 24d and reusable patient line 26, respectively, are removed or not connected to the connectors.

FIG. 1 also illustrates that housing 22 provides a drain line connector 34, which may be releasably covered by a moveable, e.g., rotatable or slideable cover 34c. Drain line connector 34 receives a disposable drain line 36 for treatment, which may run to a drain container or bag or to a house drain. Disposable drain line 36 is disconnected from drain line connector 34 during disinfection.

Disposable PD fluid or solution containers or bags (not illustrated because system 10 is in a disinfection configuration with the containers or bags removed) are connected respectively to reusable PD fluid supply lines 24a to 24d. Distal ends 24e of reusable PD fluid supply lines 24a to 24d may be color coded and/or keyed to match a colored or keyed connector of a dedicated PD fluid container or bag. The containers or bags may hold the same or different dextrose or glucose level PD fluids, such as 1.36% glucose PD fluid, 2.27% glucose PD fluid, 3.86% glucose PD fluid and/or a last bag of a different formulation of PD fluid, such as icodextrin.

It should be appreciated that any number of reusable PD fluid supply lines 24a to 24d and PD fluid containers or bags may be provided, including a single reusable PD fluid line and PD fluid container or more than one reusable PD fluid lines and PD fluid containers. In a further alternative embodiment, the PD fluid containers or bags are replaced by an online PD fluid generation source, which connects to and communicates fluidly with a single reusable PD fluid supply line.

Besides disposable drain line 36 (and associated container if used) and the disposable PD fluid containers or bags, it is contemplated that in one embodiment, the only other disposable component of system 10 is a disposable filter set (not illustrated) removably connected by the patient at the distal end 26d of reusable patient line 26 to provide a final stage of PD fluid filtration prior to delivery to the patient. In an embodiment, the disposable filter set is spliced between the distal end 26d of reusable patient line 26 and the patient's transfer set, which leads to an indwelling PD catheter inserted into the patient.

It is contemplated that any one, or more, or all of reusable PD fluid supply lines 24a to 24d, reusable patient line 26, disinfection connectors 30a to 30d, patient line connector 32, drain line connector 34, drain line 36, the PD fluid containers or bags and the patient line filter set be made of any one or more plastic, e.g., polyvinylchloride ("PVC") or a non-PVC material, such as polyethylene ("PE"), polyurethane ("PU"), polypropylene ("PP") or polycarbonate ("PC").

FIG. 1 further illustrates that reusable supply tube 52a runs from each reusable PD fluid supply line 24a to 24d, via a PD fluid supply valve 54a to 54d, respectively, to a PD fluid inline heater 56. In an embodiment, each of the valves of APD cycler 20, including PD fluid supply valves 54a to 54d, is an electrically actuated valve having a reusable valve body that occludes (e.g., when unpowered for fail safe operation) or allows (e.g., when powered) PD fluid to flow through the body. In the illustrated embodiment, valve 54d is a three-way valve having a normally open port for receiving PD fluid from reusable PD fluid supply line 24b or 24c and a normally closed port for receiving PD fluid from reusable PD fluid supply line 24d. PD fluid inline heater 56 is also electrically actuated in one embodiment and is, for example, a resistive heater having a reusable heater body that accepts PD fluid for treatment and for disinfection heating. Inline heater 56 in an embodiment is able to heat PD fluid from room temperature or colder (e.g., if the PD fluid is stored in a cold environment) to body temperature, e.g., 37° C., at a flowrate of up to at least 200 milliliters ("ml")/minute.

A first temperature sensor 58a is located adjacent to inline heater 56, e.g., downstream from the heater to provide feedback for temperature control. If desired, a second temperature sensor (not illustrated) may be provided upstream from PD fluid heater 56 to enable the incoming temperature of fresh PD fluid to be taken into account for the heating algorithm. A second temperature sensor 58b is illustrated just downstream from PD fluid pump 70, which is provided for example as a second check that fresh PD fluid exiting PD fluid pump 70 is at a desired temperature for treatment, e.g., body temperature or 37° C.

In the illustrated embodiment, a flow switch 68 is located just upstream from PD fluid inline heater 56. An output from flow switch 68 is used to make sure there is PD fluid flow through inline heater 56. If the output (or lack thereof) from flow switch 68 indicates no or little PD fluid flow, which could be harmful to inline heater 56 if powered, causes system 10 to halt power to inline heater 56 and to stop treatment or disinfection if needed while (i) attempting to find a remedy to the no or low flow situation or (ii) causing an audio, visual or audiovisual alarm or alert at user interface 108. Alternative ways for ensuring flow to the inline heater 56 in order to power the heater may be used alternatively.

Reusable tube 52b runs from the outlet of PD fluid inline heater 56 to an airtrap 60 in the illustrated embodiment of FIG. 1. Any of the reusable tubing inside the housing of cycler 20, including reusable tubes 52a and 52b, may be made of metal, e.g., stainless steel or plastic, e.g., polyvinylchloride ("PVC") or a non-PVC material, such as polyethylene ("PE"), polyurethane ("PU"), polypropylene ("PP"), polyether ether ketone ("PEEK"), or polycarbonate ("PC"). In an embodiment, one or more level sensor 62a and 62b is located adjacent airtrap 60, so that a desired level or range of levels of PD fluid is/are maintained in the airtrap. A fluid line valve 54e is located downstream from airtrap 60 in the illustrated embodiment and receives fresh, heated PD fluid from the airtrap. A gas line valve 54g is located along a gas line 52g extending from a top of airtrap 60. Airtrap 60 may be closed upstream by PD fluid supply valves 54*a* to 54*d* to drain the airtrap when dictated by the output of level sensor 62*a* or 62*b*.

A reusable fluid line 52*c* and gas line 52*g* run between fluid line valve 54*e* and gas line valve 54*g*, respectively, and a PD fluid pump 70 located within housing 22 of cycler 20. PD fluid pump 70 includes a reusable pump body that accepts PD fluid for pumping. That is, pump 70 does not require the PD fluid to flow within a disposable item, such as a tube or cassette. The reusable pump body of pump 70 itself accepts the PD fluid. PD fluid pump 70 may be of a type, e.g., piston pump, which is inherently accurate so that a separate PD fluid volume measurement apparatus, such as a balance chamber or flowmeter, is not needed. PD fluid pump 70 may alternatively be a less accurate gear or centrifugal pump that does operate with a PD fluid volume measurement apparatus. PD fluid pump 70 is controllable to pump to and from the patient at or below a pressure limit by controlling a level of current to the PD fluid pump. A positive patient pressure limit may for example be one to five psig (e.g., two psig (14 kPa)). A negative patient pressure limit may for example be −1.0 psig to −3.0 psig (e.g., −1.3 psig (−9 kPa)). PD fluid pump 70 is also capable of supplying lower pressures if needed, e.g., for small children or babies. PD fluid pump 70 is bidirectional and continuous in one embodiment, such that a single pump may be provided.

FIG. 1 further illustrates that a fresh PD fluid patient line valve 54*f* is located in an embodiment along reusable fresh PD fluid patient tube or line 52*f* between downstream temperature sensor 58*b* and spool or hose reel 28. Fresh PD fluid patient tube or line 52*f* communicates fluidly with a fresh PD fluid lumen of dual lumen reusable patient line 26 in one embodiment. A used PD fluid patient line valve 54*u* is located in an embodiment along reusable used PD fluid patient tube or line 52*u* between PD fluid pump 70 (via cross 64*a*) and spool or hose reel 28. Used PD fluid patient tube or line 52*u* communicates fluidly with a used PD fluid lumen of dual lumen reusable patient line 26 in one embodiment. A drain line valve 54*h* is located along reusable drain tube or line 52*h* that extends from a tee 66 to drain line connector 34.

A first patient pressure sensor 72*a* is located along fresh PD fluid patient tube or line 52*f* between PD fluid pump 70 and spool or hose reel 28 to measure positive patient PD fluid pressure. A second patient pressure sensor 72*b* is located along gas line 52*g* to measure negative patient PD fluid pressure during a patient drain (gas is at same negative pressure as used PD fluid via fluid communication at cross 64*a*). Third and fourth pressures sensor 72*c* and 72*d* are located along reusable disinfection tube or line 52*d*.

As discussed above, patient line connector 32 is located at APD cycler housing 22 and accepts dual lumen reusable patient line 26 during disinfection and generally while the patient is not undergoing treatment. Patient line connector 32 in one embodiment includes a sealed fluidic U-turn or 180 degree turn that allows disinfection fluid, e.g., heated PD fluid, to flow from one lumen of the dual lumen patient line to another lumen of the dual lumen patient line. Dual lumen reusable patient line 26 is therefore included in the disinfection loop.

As further discussed above, drain line 36 is flexible and disposable in one embodiment and connects to drain line connector 34 extending from housing 22 of APD cycler 20 during treatment. After treatment, drain line 36 may be removed during the disinfection sequence. Drain line connector 34 receives an internal, reusable drain tube or line 52*h* for delivering used PD fluid to drain line 36 during a patient drain. Drain line connector 34 also receives vent tube or line 52*v* for delivering gas, such as air or carbon dioxide ($CO_2$), to drain line 36 during treatment. A vent valve 54*v* is located along vent tube or line 52*v*.

A reusable disinfection tube or line 52*d* as illustrated in FIG. 1 extends to a second cross 64*b* along with vent tube or line 52*v* and used PD fluid patient tube or line 52*u*. Reusable disinfection tube or line 52*d* includes a disinfection valve 54*s*. Disinfection tube or line 52*d* handles disinfection fluid, e.g., fresh, heated PD fluid, vent tube or line 52*v* handles vented gas, e.g., air, while used PD fluid patient tube or line 52*u* handles used PD fluid during treatment.

A bypass line 52*y* as illustrated in FIG. 1 is located between disinfection connectors 30*c* and 30*d* for use during disinfection. A similar bypass line 52*z* is provided between disinfection connectors 30*a* and 30*b*. During disinfection, heated disinfection fluid, such as PD fluid, is directed through bypass lines 52*y* and 52*z* to fully disinfect disinfection connectors 30*a* to 30*d*.

FIG. 1 also illustrates that system 10 includes a carbon dioxide ($CO_2$) source 80, which may be connected fluidly to the disinfection loop for example between PD fluid pump 70 and pressure sensor 72*a*, e.g., via $CO_2$ line 52*o*. A $CO_2$ valve 54*o* is located along $CO_2$ line 52*o*. As discussed in detail below, system 10 causes a desired and efficient amount of $CO_2$ gas to be metered from $CO_2$ source 80 into the disinfection fluid, e.g., PD fluid, just prior to disinfection to prevent and/or remove any build-up of calcium carbonate ($CaCO_3$) as the PD fluid is heated. $CO_2$ source 80 may for example be initially pressurized to 70 kPa (10 psig) to provide ample pressure over multiple disinfection sequences according to the pressurization scheme discussed herein.

FIG. 1 further illustrates that a gas or $CO_2$ pressure regulator 74 and a $CO_2$ pressure sensor 76 may optionally be located along $CO_2$ line 52*o* upstream from $CO_2$ valve 54*o*. $CO_2$ pressure regulator 74 enables $CO_2$ source 80 to be pressurized to a higher level so that is lasts longer. Regulator 74 then regulates the high incoming pressure from $CO_2$ source 80 down to a smoothly outputted desired output pressure. The desired operating pressure for example may be slightly above the pressures (or pressure increases) to be achieved, which are obtained from table 110 or table 120 as discussed below in connection with FIGS. 6 and 7, respectively. $CO_2$ pressure sensor 76 reads and outputs a pressure corresponding to the $CO_2$ pressure remaining within $CO_2$ source 80. A one-way or check valve 78 may also be provided and oriented so as to prevent fresh or used PD fluid from entering $CO_2$ line 52*o*.

FIG. 1 still further illustrates that APD cycler 20 of system 10 of the present disclosure includes a control unit 100 having one or more processor 102 and one or more memory 104 that receive, store and process signals or outputs from the pressure sensors 72*a* to 72*d*, $CO_2$ pressure sensor 76 if provided, temperature sensors 58*a* and 58*b*, flow switch 68 and possibly a conductivity sensor (not illustrated). Control unit 100 uses pressure feedback from pressure sensors 72*a* and 72*b* to control PD fluid pump 70 to pump fresh and used PD at safe patient and system pressure limits. Control unit 100 uses temperature feedback from temperature sensor 58*a* to control inline PD fluid heater 56 to heat the fresh PD fluid to, e.g., body temperature or 37° C. for treatment, and to 85° C. for disinfection. Control unit 100 uses flow switch feedback from flow switch 68 to determine whether to power PD fluid inline heater 56. Control unit 100 as discussed herein further uses feedback from pressure sensor 72a (and perhaps pressure sensor 72b) to determine how much $CO_2$ has been delivered to a disinfection loop via $CO_2$ line 52o.

Control unit 100 as illustrated in FIG. 1 also includes a video controller 106 that interfaces with a user interface 108, which may include a display screen operating with a touchscreen and/or one or more electromechanical button, such as a membrane switch. User interface 108 may also include one or more speaker for outputting alarms, alerts and/or voice guidance commands. User interface 108 may be provided with cycler 20 as illustrated in FIG. 1 and/or be a remote user interface operating with control unit 100. Control unit 100 may also include a transceiver (not illustrated) and a wired or wireless connection to a network, e.g., the internet, for sending treatment data to and receiving prescription instructions from a doctor's or clinician's server interfacing with a doctor's or clinician's computer.

Control unit 100 opens and closes PD fluid valves 54a to 54h, 54o, 54s, 54u and 54v in combination with the operation of PD fluid pump 70 and inline heater 56 to run a pre-priming sequence, multiple patient fill sequences, multiple patient drain sequences, and a disinfection sequence after a PD treatment. The disinfection sequence readies APD cycler 20 for the next treatment. In an embodiment, remaining fresh PD fluid is heated after the final patient drain and is used as the disinfection fluid for disinfection.

To form a disinfection loop 90 for the disinfection sequence, each reusable PD fluid supply line 24a to 24d is connected to a respective disinfection connector 30a to 30d, reusable patient line 26 is connected to reusable patient line connector 32, and drain line 36 is removed in one embodiment, so that drain line connector 34 may close shut. As illustrated in FIG. 1, disinfection loop 90 includes patient line connector 32 (including its U-turn or 180 degree turn), both lumens of reusable dual lumen patient line 26, used PD fluid patient tube or line 52u, reusable disinfection tube or line 52d, reusable drain tube or line 52h, vent tube or line 52v, drain line connector 34, reusable PD fluid supply lines 24a to 24d, bypass lines 52y, 52z, and reusable tubes or lines 52a to 52c and 52f. Disinfection loop 90 also includes the insides of all flow components and fluid-contacting sensors located along the above-listed lines.

Control unit 100 may sequence certain of the valves along disinfection loop 90 during disinfection. For example, PD fluid supply valve 54a may be sequenced open and closed during disinfection to allow disinfection fluid to flow through supply valve 54a or be forced completely through reusable PD fluid supply line 24a. Control unit 100 may also cause PD fluid pump 70 to run sequentially in forward and reverse states during disinfection, so that the disinfection fluid may flow clockwise and counterclockwise through disinfection loop 90. Control unit 100 also causes inline heater 56 to heat the disinfection fluid, e.g., fresh PD fluid, to a desired disinfection temperature, such as 70° C. to 95° C.

The use of PD fluid containing bicarbonate as a disinfection fluid likely leads to the formation of calcium carbonate ($CaCO_3$) in the disinfected flowpaths and flow components of disinfection loop 90 of PD machine or cycler 20. Carbon dioxide ($CO_2$) from source 80 is provided accordingly just prior to disinfection to prevent and/or to remove the formation of calcium carbonate. FIGS. 2 to 5 illustrate a simplified version of disinfection loop 90, showing important components to the $CO_2$ injection from source 80, including PD fluid inline heater 56, first temperature sensor 58a, PD fluid pump 70, fresh PD fluid patient pressure sensor 72a, $CO_2$ source 80, $CO_2$ line 52o, $CO_2$ valve 54o and control unit 100. It should be appreciated however that the sequences described in connection with FIGS. 2 to 5 are equally applicable to the full disinfection loop 90 of PD machine or cycler 20 of system 10 in FIG. 1.

Lookup Table Based on Bicarbonate Level and/or Disinfection Temperature

Figure 4:
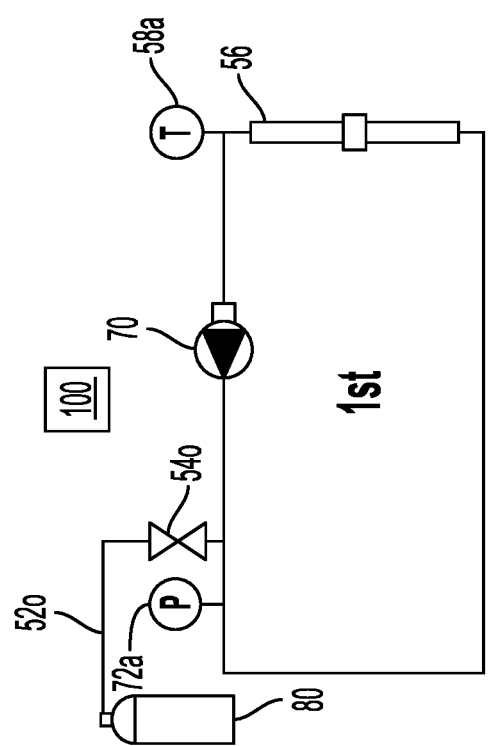
FIG. 4 is a simplified schematic view of one embodiment of an automated peritoneal dialysis ("APD") machine or cycler of the present disclosure pumping heated PD disinfection fluid containing delivered $CO_2$ during disinfection.
Figure 5:
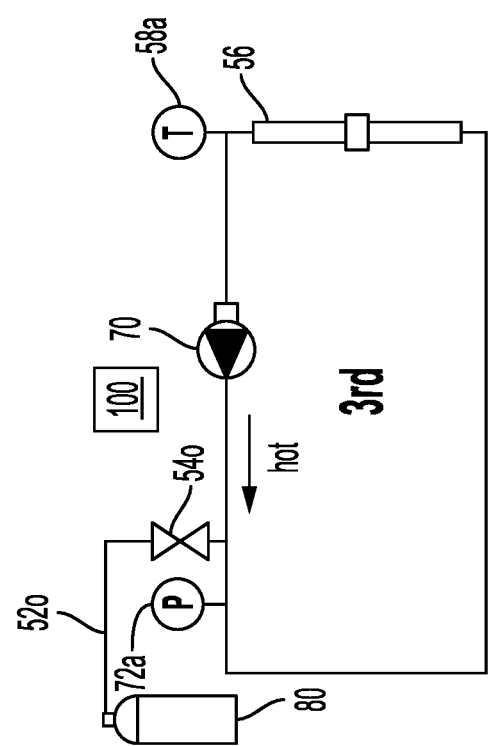
FIG. 5 is a simplified schematic view of one embodiment of an automated peritoneal dialysis ("APD") machine or cycler of the present disclosure optionally delivering $CO_2$ to the disinfection loop during a cool down period.
Figure 6:
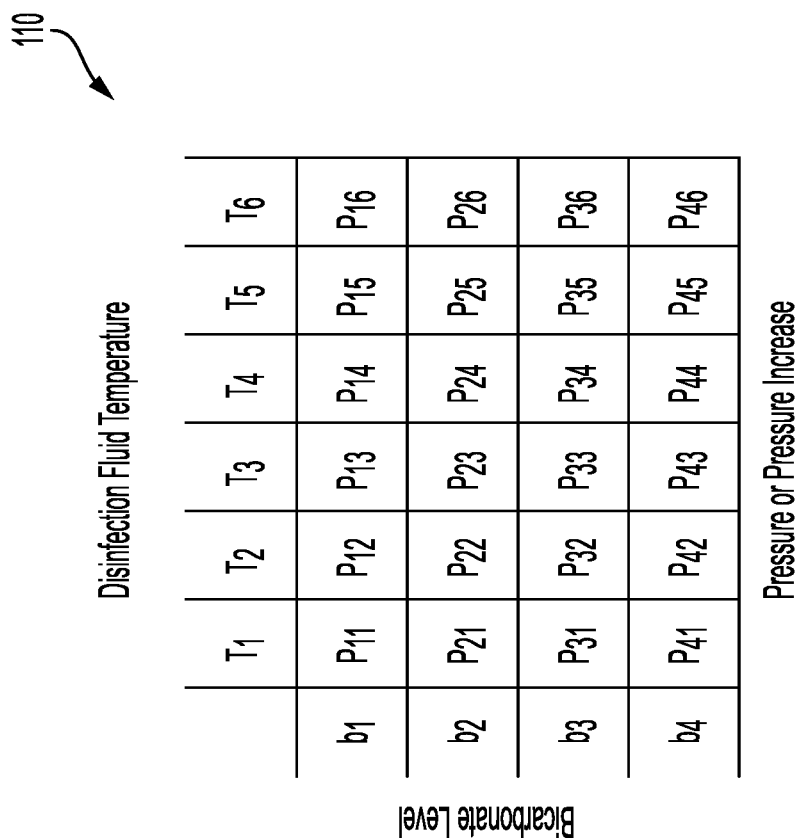
FIG. 6 is an example lookup table stored in a control unit of an automated peritoneal dialysis ("APD") machine or cycler of the present disclosure, the lookup table providing a pressure to achieve, or a pressure increase, due to $CO_2$ injection, wherein the pressure is based on at least one of an amount of bicarbonate in the PD disinfection fluid and/or a disinfection fluid temperature.

Referring now to FIG. 6, the sequences of FIGS. 2 to 5 in an embodiment rely on a table 110 (or corresponding algorithm) stored in one or more memory 104 of control unit 100, which sets a pressure to achieve, or a pressure increase, due to the injection of $CO_2$ based on at least one of a bicarbonate level in the PD disinfection fluid or a disinfection fluid temperature. As illustrated in FIG. 6, table 100 sets a pressure increase due to the $CO_2$ injection or an overall pressure to be achieved ($P_{11}$ to $P_{46}$) by the $CO_2$ injection as a function of at least one of solution bicarbonate composition ($b_1$ to $b_4$) and disinfection fluid temperature setting ($T_1$ to $T_6$). FIG. 6 accordingly illustrates the pressure (or pressure increase) to achieve as a function of both bicarbonate level and disinfection fluid temperature setting in a two dimensional array. FIG. 6 could alternatively however base the pressure (or pressure increase) to achieve as a function of only one of bicarbonate level or disinfection fluid temperature Generally, the more bicarbonate present in the fresh PD fluid, the higher the pressure in table 110 needed due to the injected $CO_2$ gas. And generally, the higher the disinfection PD fluid temperature, the higher the pressure in table 110 needed due to the injected $CO_2$ gas. To populate table 110, experiments and/or calculations are performed varying bicarbonate levels against varied disinfection fluid temperatures to determine how much $CO_2$ gas pressure is needed to effectively block the formation of calcium carbonate precipitation, while efficiently using $CO_2$ gas, so as not to waste $CO_2$, and so that the $CO_2$ source 80 may be of a reasonable size, while still providing many disinfection sequence's worth of $CO_2$.

Control unit 100 at the beginning of each disinfection sequence knows the bicarbonate level from the prescribed PD fluid used for the just-ended treatment. Control unit 100 also knows and sets the disinfection fluid temperature, which may be the same or be different for different disinfection sequences. Control unit 100 accesses table 110 (or corresponding algorithm) and finds the operating pressure (or pressure increase) to achieve based on the known bicarbonate level and the known disinfection fluid temperature. It should be appreciated that table 110 could alternatively compare disinfection fluid temperature against the type of bicarbonate-based PD fluid used, which is basically the same as comparing disinfection fluid temperature against bicarbonate level. It should also be appreciated that PD fluids not containing bicarbonate do not have the precipitation issues discussed herein. So when using a PD fluid for disinfection that does not contain bicarbonate, control unit 100 does not access table 110 and does not inject $CO_2$ gas from $CO_2$ source 80.

Lookup Table Based on Mole Fraction

Figure 7:
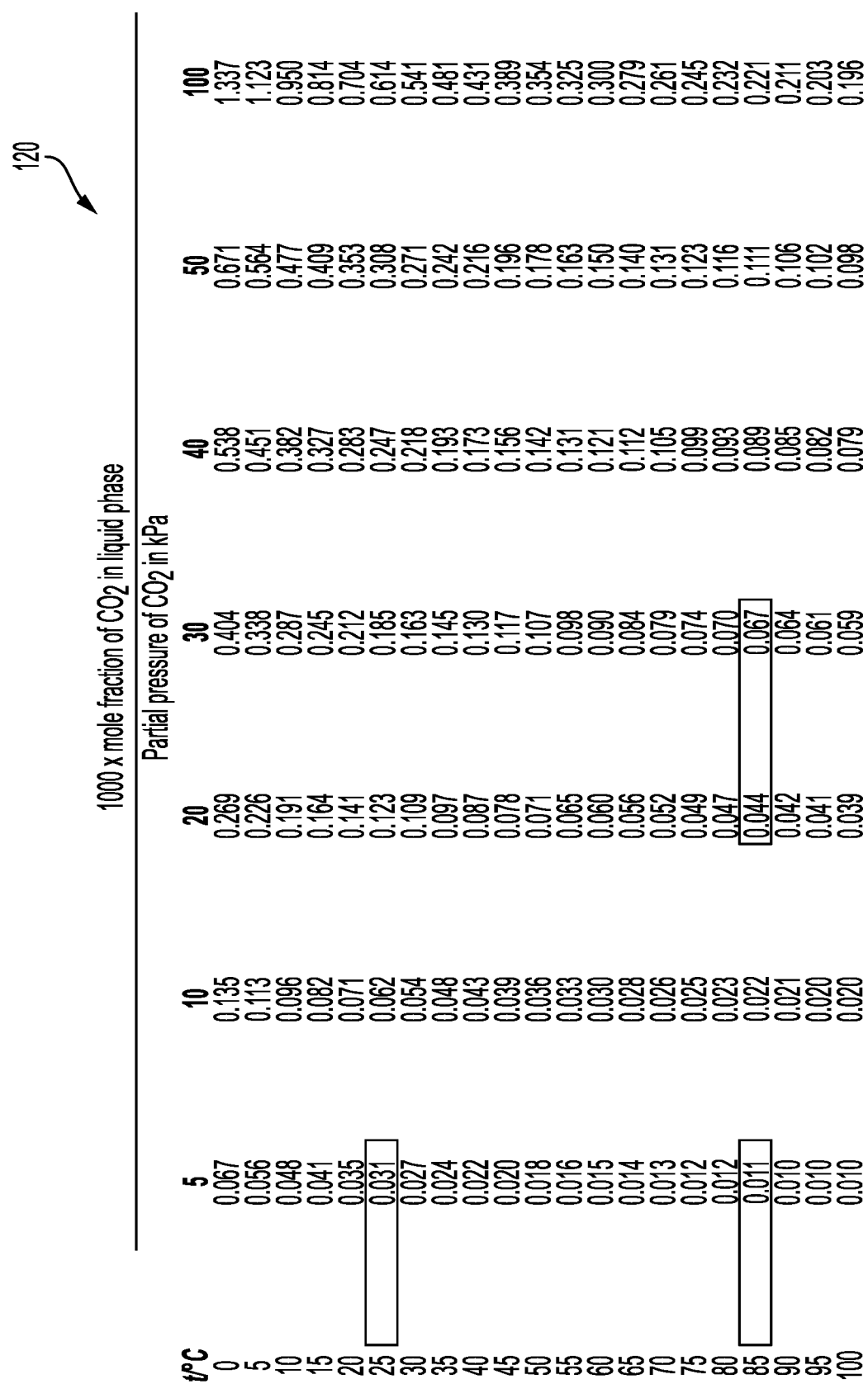
FIG. 7 is an example alternative lookup table stored in a control unit of an automated peritoneal dialysis ("APD") machine or cycler of the present disclosure, the lookup table providing a pressure to achieve, or a pressure increase, due to $CO_2$ injection, wherein the pressure is based on a mole fraction of $CO_2$.

Referring now to FIG. 7, the sequences of FIGS. 2 to 5 in an alternative embodiment rely on a table 120 (or corresponding algorithm) stored in one or more memory 104 of control unit 100, which uses a mole fraction of $CO_2$. Table 120 of FIG. 7 represents the mole fraction of $CO_2$, which depends on the type of disinfection fluid, e.g., type of PD fluid, PD fluid temperature (left-hand column, ° C.) and PD fluid pressure (upper row, kPA), wherein the mole fraction values populate the spaces corresponding to a given temperature and pressure. In an embodiment, a separate table (like table 120) is stored and is accessible by control unit 100 for each possible disinfection fluid or PD fluid, e.g., one for 1.36% glucose PD fluid, another for 2.27% glucose PD fluid and a third for 3.86% glucose PD fluid.

In one example for using a table 120 in FIG. 7, the following information is taken as being known and may be stored (or a portion thereof) in control unit 100:
- disinfection loop 90 volume is 200 ml
- $CO_2$ source 80 holds 18 g of $CO_2$
- $CO_2$ molar mass is 44.01 g/mol
- $CaCO_3$ molar mass is 100.0869 g/mol
- disinfection fluid molar mass (assume that of $H_2O$) is 18.02 g/mol
- disinfection fluid $H_2O$ density (assume that of $H_2O$) is 0.96859 g/ml
- calcium content (Ca)' of disinfection fluid is 1.25 mmol/L)

On a per disinfection sequence basis using the following chemical reaction for eliminating calcium carbonate, where $H_2CO_3$ is carbonic acid and $HCO_3$ is bicarbonate, and wherein $H_2O$ is obtained from the PD fluid used for disinfection:

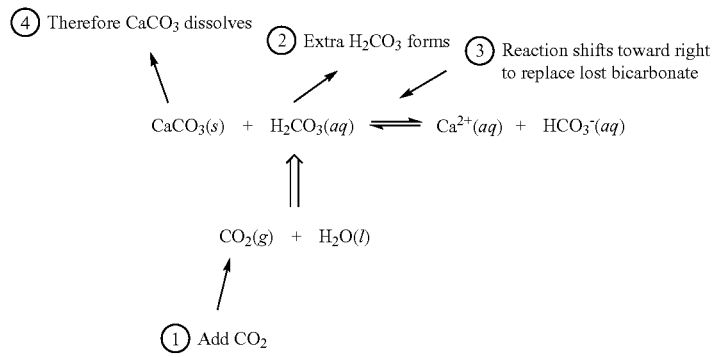

max $CaCO_3 = 1.25 \times 0.2$ mmol $= 0.25$ mmol $\rightarrow 0.25e^{-3} \times 100.0869$ g $= 0.025021725$ g $CaCO3$ 1 mmol $Ca^{2+} \rightarrow 2$ mmol $H^+$ needed $CO_2 = 2 \times$ mmol $CaCO_3 = 0.5$ mmol $CO_2 \rightarrow 0.5e^{-3} \times 44.01$ g $= 0.022005$ g $CO_2$ one tank of 18 g $CO_2$ with an effective use of 45% $\rightarrow$ 18/0.022005$\times$0.45$=$368 cycles of $CO_2$ A goal of the $CO_2$ injection is to increase the pressure measured by pressure sensor 72*a*, so that dissolved $CO_2$ is maintained during the heated disinfection sequence at a predetermined amount calculated above to be 0.5 mmol. An assumption that the source of PD fluid used for disinfection, e.g., a bag of such fluid, is in equilibrium with the ambient surroundings regarding temperature and pressure is made, such that the initial partial pressure of $CO_2$ may be assumed to be roughly 0.04 kPa (partial pressure of $CO_2$ at ambient). Using table 120 of FIG. 7, and extrapolating from the 0.031 molar fraction valve at 5 kPa and 25° C. yields about 0.00031 molar fraction of $CO_2$ at normal ambient conditions ((0.04 kPa/5 kPa) is roughly 1/10 of 0.031, which equals 0.00031 molar fraction).

In the example it is also assumed (and would be known in a commercial implementation) that the volume of disinfection or PD fluid circulated in disinfection loop 90 is 200 milliliters ("ml"). Knowing the density of the PD disinfection fluid (using density of water in the example), 200 ml of PD fluid equals 193.72 grams or 10.75 mols of the fluid in disinfection loop 90. At normal ambient conditions (5 kPa and 25° C.) 10.75 mols$\times$0.00031 molar fraction yields 0.0033 mmols of $CO_2$, which drops to 0.0012 mmols $CO_2$ at 85° C. (0.00011 molar fraction$\times$10.75 mols) as extrapolated from table 120 of FIG. 7 for 0.04 kPa at 85° C., which is a typical disinfection temperature. The drop dictates that 0.5012 (0.0012+0.5) mmols of $CO_2$ needs to be injected into the heated PD fluid. 0.5012 (0.0012+0.5) mmols of $CO_2$ in turn yields a needed molar fraction of 0.5012/10.75=0.0466, which in turn yields a partial pressure increase of about 21 kPa (3 psig) at 85° C. according to table 120 of FIG. 7.

Using the table 120 of FIG. 7 and the above knowns based on solid assumptions, which are programmed into control unit 100, control unit 100 can thereby calculate for a given PD fluid to be used as a disinfecting fluid, and a given disinfection temperature (each of which may be programmed into control unit 100 at the time of treatment, or be known from a patient's prescription), the pressure at which the disinfecting PD fluid needs to be increased via $CO_2$ pressure from source 80, wherein the pressure is set in one embodiment by downstream $CO_2$ pressure regulator 74.

$CO_2$ Injection Steps

Figure 2:
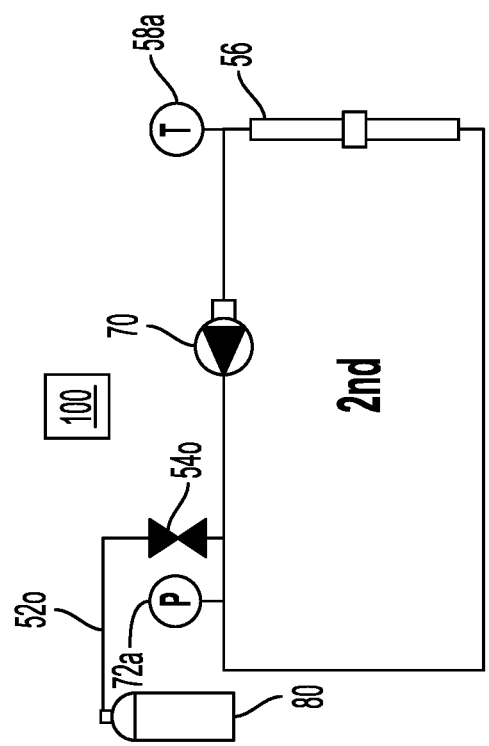
FIG. 2 is a simplified schematic view of one embodiment of an automated peritoneal dialysis ("APD") machine or cycler of the present disclosure after treatment and prior to disinfection.

FIG. 2 illustrates a first step in which a PD treatment has been completed and it is time for control unit 100 to perform disinfection. Prior to beginning the disinfection sequence, control unit 100 in one embodiment, with $CO_2$ valve 54*o* closed (not shaded), PD fluid pump 70 not actuated and inline heater 56 unenergized, finds the pressure (or pressure increase) to be achieved from table 110 of FIG. 6 based on a known bicarbonate level and/or disinfection temperature. Control unit 100 in an alternative embodiment, with $CO_2$ valve 54*o* closed, PD fluid pump 70 not actuated and inline heater 56 unenergized, takes initial pressure and temperature measurements via pressure sensor 72*a* and temperature sensor 58*a*, respectively, to obtain an initial $CO_2$ mole fraction value from the table 120 of FIG. 7. An optional pH sensor or $CO_2$ sensor (not illustrated) may be provided and used alternatively or additionally to determine the initial $CO_2$ mole fraction, however, the table 120 of FIG. 7 for the disinfection fluid will suffice and eliminates the need for extra sensors.

Figure 3:
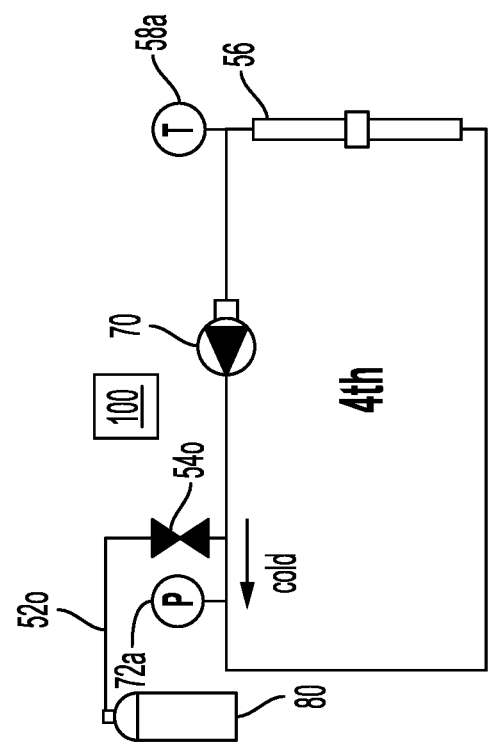
FIG. 3 is a simplified schematic view of one embodiment of an automated peritoneal dialysis ("APD") machine or cycler of the present disclosure delivering $CO_2$ to a disinfection loop.

FIG. 3 illustrates a second step in which control unit 100, with PD fluid pump 70 not actuated and inline heater 56 unenergized, causes $CO_2$ valve 54o to open (valve shaded), allowing $CO_2$ to be injected into the PD fluid within disinfection loop 90. Control unit 100 may pulse $CO_2$ or inject the $CO_2$ continuously, but in either case control unit 100 monitors the output of pressure sensor 72a and stops injecting $CO_2$ when the pressure achieves the needed pressure (or pressure increase (e.g., about 21 kPa (3 psig) at 85° C.)) from table 110 of FIG. 6 or table 120 of FIG. 7.

FIG. 4 illustrates a third step in which control unit 100 causes inline heater 56 to be energized and PD fluid pump 70 to circulate heated, disinfection fluid (PD fluid) about disinfection loop 90 in any of the alternative manners described above and at the elevated pressure obtained in FIG. 3. Heated disinfection fluid circulation takes place for a designated amount of time. During this time, the presence of the designated amount of $CO_2$ at the elevated pressure prevents or removes calcium carbonate ($CaCO_3$) according to the chemical reaction shown above. It should be appreciated that while $CO_2$ valve 54o is shown as being closed (not shaded) in FIG. 4, in an alternative embodiment, control unit 10 may cause $CO_2$ valve 54o to be opened so as to allow $CO_2$ gas to be injected into disinfection loop 90 during a part or all of the heat disinfection.

FIG. 5 illustrates a fourth and perhaps optional step in which control unit 100 causes inline heater 56 to de-energize but continues to allow fluid pump 70 to circulate cooled-down PD fluid. During a cool down period, control unit 100 monitors the output of pressure sensor 72a to see if the output returns to the pressure level prior to heating in FIG. 4. If perhaps some leakage of $CO_2$ has occurred and the pressure falls below the $CO_2$ injected pressure at the end of FIG. 3, then control unit 100 may cause $CO_2$ valve 54o to open (valve shaded) to allow additional $CO_2$ to be injected, e.g., so as to re-reach the needed pressure increase (e.g., about 21 kPa (3 psig)) above the initial, starting pressure. The ammonia and/or $CO_2$ sensor if provided may be used additionally or alternatively here. Note that the cooled-down PD fluid will have a higher mole fraction of $CO_2$, such that the $CO_2$ pressure will not need to be increased to the earlier level, e.g., to 21 kPa.

Control unit 100 in one embodiment causes valves 54e, 54f, 54g, 54h and 54u to be closed and $CO_2$ valve 54o to open, so that PD fluid patient tube or line 52f is pressurized with $CO_2$ gas to whatever pressure remains within $CO_2$ source 80. Here, first patient pressure sensor 72a reads the pressure remaining within $CO_2$ source 80 and sends a corresponding signal to control unit 100. In an alternative embodiment illustrated in FIG. 1, $CO_2$ pressure sensor 76 is provided upstream from pressure regulator 74 so as to be able to read the pressure remaining within $CO_2$ source 80 and send a corresponding signal to control unit 100. In either situation, control unit 100 in an embodiment is configured to send a message to a central location when it determines that the pressure level within $CO_2$ source 80 is running low, so that a new $CO_2$ source 80 may be ordered and delivered to the patient. User interface 108 may also provide an audio, visual or audiovisual message to the patient that $CO_2$ source 80 is running low but that a new supply is on the way. Upon the patient receiving the new $CO_2$ source 80, user interface 108 may also provide an audio, visual or audiovisual instructions to the patient as to how to replace the existing $CO_2$ source 80 with a new $CO_2$ source 80.

It should be understood that various changes and modifications to the presently preferred embodiments described herein will be apparent to those skilled in the art. It is therefore intended that such changes and modifications be covered by the appended claims. For example, while FIGS. 2 to 5 illustrate readings being taken from a single pressure sensor and temperature sensor, control unit 100 may alternatively analyze pressure and temperature outputs from multiple pressure and temperature sensors located at different locations along disinfection loop 90. As noted herein, the pressures listed in tables 110 and 120 of FIGS. 6 and 7, respectively, may be absolute pressure values or pressure increase or pressure delta values.

The invention is claimed as follows:

1. A peritoneal dialysis ("PD") system comprising:
a PD fluid pump;
a disinfection loop including the PD fluid pump, the disinfection loop including PD fluid used for disinfecting the disinfection loop; and
a carbon dioxide ($CO_2$) source positioned and arranged to supply $CO_2$ to the disinfection loop to inhibit the production of and/or remove calcium carbonate ($CaCO_3$) during a disinfection sequence.

2. The PD system of claim 1, which includes a $CO_2$ valve located between the disinfection loop and the $CO_2$ source, the $CO_2$ valve opened to allow the $CO_2$ to be supplied to the disinfection loop.

3. The PD system of claim 2, which includes a control unit configured to cause the $CO_2$ valve to open to allow the $CO_2$ to pressurize the PD fluid to a desired pressure or pressure increase to inhibit the production of and/or remove calcium carbonate during the disinfection sequence.

4. The PD system of claim 3, which includes at least one pressure sensor outputting to the control unit, the control unit configured to monitor the at least one pressure sensor output to detect the desired pressure or pressure increase.

5. The PD system of claim 3, wherein the control unit is configured to use a lookup table to determine the desired pressure or pressure increase.

6. The PD system of claim 5, wherein the control unit stores a disinfection temperature to which the PD fluid is heated for the disinfection sequence, and wherein the desired pressure or pressure increase in the lookup table corresponds to the disinfection temperature.

7. The PD system of claim 6, which includes at least one temperature sensor outputting to the control unit, the control unit configured to monitor the at least one temperature sensor output to detect the disinfection temperature.

8. The PD system of claim 5, wherein the lookup table is specific to the type of PD fluid used for disinfection.

9. The PD system of claim 5, wherein the control unit knows a bicarbonate level for the PD fluid used for disinfection, and wherein the desired pressure or pressure increase in the lookup table corresponds to the bicarbonate level.

10. The PD system of claim 5, wherein the control unit is configured to take initial pressure and temperature readings prior to supplying $CO_2$ to the disinfection loop, the control unit further configured to determine the initial amount of $CO_2$ contained in the disinfection loop using the lookup table and the initial pressure and temperature readings.

11. The PD system of claim 3, wherein the control unit is configured to use an algorithm to determine the desired pressure or pressure increase.

12. The PD system of claim 3, wherein the control unit is configured to cause the $CO_2$ valve to open to allow the $CO_2$ to pressurize the PD fluid to the desired pressure or pressure increase prior to causing the PD fluid pump to run during the disinfection sequence.

13. The PD system of claim 3, wherein the control unit is configured to cause the $CO_2$ valve to open to allow the $CO_2$ to pressurize the PD fluid to the desired pressure or pressure increase while causing the PD fluid pump to run during the disinfection sequence.

14. The PD system of claim 3, which includes a PD fluid heater, and wherein the control unit is configured to cause the $CO_2$ valve to open to allow the $CO_2$ to pressurize the PD fluid to the desired pressure or pressure increase prior to causing the PD fluid heater to heat the PD fluid during the disinfection sequence.

15. The PD system of claim 3, which includes a PD fluid heater, and wherein the control unit is configured to cause the $CO_2$ valve to open to allow the $CO_2$ to pressurize the PD fluid to the desired pressure or pressure while causing the PD fluid heater to heat the PD fluid during the disinfection sequence.

16. The PD system of claim 3, wherein the control unit is configured to cause the $CO_2$ valve to open to allow the $CO_2$ to pressurize the PD fluid during a cool down period if a loss of pressure is detected by the control unit.

\* \* \* \* \*